(12) United States Patent
Lignell et al.

(10) Patent No.: US 6,773,708 B1
(45) Date of Patent: Aug. 10, 2004

(54) USE OF XANTHOPHYLLS, ASTAXANTHIN E.G., FOR TREATMENT OF AUTOIMMUNE DISEASES, CHRONIC VIRAL AND INTRACELLULAR BACTERIAL INFECTIONS

(75) Inventors: Åke Lignell, Värmdö (SE); Per Böttiger, Saltsjö-boo (SE)

(73) Assignee: AstaReal AB, Gustavsberg (SE)

( * ) Notice: Subject to any disclaimer, the term of this patent is extended or adjusted under 35 U.S.C. 154(b) by 0 days.

(21) Appl. No.: 10/088,496

(22) PCT Filed: Oct. 5, 2000

(86) PCT No.: PCT/SE00/01923

§ 371 (c)(1),
(2), (4) Date: Mar. 28, 2002

(87) PCT Pub. No.: WO01/24787

PCT Pub. Date: Apr. 12, 2001

(30) Foreign Application Priority Data

Oct. 7, 1999 (SE) ................................ 9903619

(51) Int. Cl.$^7$ ................................ A61K 35/78
(52) U.S. Cl. .................... 424/195.17; 514/725
(58) Field of Search ...................... 424/195.17; 514/725

(56) References Cited

U.S. PATENT DOCUMENTS 5,744,502 A * 4/1998 Lignell et al.
5,811,446 A * 9/1998 Thomas
5,886,053 A * 3/1999 Schmutzler et al.

OTHER PUBLICATIONS

STN International, File CA, Chemical abstracts, vol. 119, No. 11, Sep. 13, 1993, (Columbus, Ohio, US), Date, Yukio et al: "Lipid peroxide–lowering compositions" & JP, A2, 05124958, 19930521, Heisei.

Nutr Cancer, vol. 26, 1996, Harumi Jyonouchi et al., "Effects of Various Carotenoids on Cloned, Effector–Stage T–Helper Cell Activity" p. 313–324.

Clinical and Diagnostic Laboratory Immunology, vol. 6, No. 3, May 1999, Sami T. Azar et al., "Type 1 (Insulin–Dependent) Diabetes is a Th1 and Th2–Mediated Autoimmune Disease", p. 306–310.

* cited by examiner

*Primary Examiner*—Francisco Prats
*Assistant Examiner*—Susan D. Coe
(74) *Attorney, Agent, or Firm*—Bacon & Thomas

(57) ABSTRACT

The use of at least one type of xanthophylls for the production of a medicament for suppression of excessive Th1 cell mediated immune responses and stimulation of Th2 cell mediated immune responses in a patient during ongoing infection and/or inflammation in said patient is disclosed. Excessive Th1 cell mediated immune responses are caused by such autoimmune diseases and chronic viral and intracellular bacterial infections as Psoriasis vulgaris, Multiple sclerosis (MS), Rheumatoid arthritis, Crohn's disease, insulin-dependent diabetes mellitus, Tuberculosis (TB), Acute graft-versus-host disease (transplant rejection) and HIV virus infection. The preferred type of xanthophyll is astaxanthin, particularly in a form esterified with fatty acids, obtainable by for example culturing the algae Haematococcus sp. Further, a method of suppressing excessive Th1 mediated immune responses and stimulating Th2 cell mediated immune responses in a patient during ongoing infection and/or inflammation in said patient is disclosed.

7 Claims, No Drawings

USE OF XANTHOPHYLLS, ASTAXANTHIN E.G., FOR TREATMENT OF AUTOIMMUNE DISEASES, CHRONIC VIRAL AND INTRACELLULAR BACTERIAL INFECTIONS

The present invention relates to the use and method of treatment concerning utilization of xanthophylls, e.g. astaxantin for suppression of excessive Th1 cell mediated immune responses and stimulation of Th2 cell mediated immune responses in a patient during ongoing infection and/or inflammation in said patient.

BACKGROUND OF THE INVENTION

CD4 T lymphocytes can be subdivided into two major subsets—Th1 cells and Th2 cells. These cells release different sets of cytokines that define their distinct actions in immunity. Th1 cells secrete interferon-gamma (IFN-γ) and are mainly involved in activating macrophages and CD8+ cytotoxic T-lymphocytes. Th2 cells secrete the interleukins Il-4, Il-5 and Il-10 and are mainly involved in stimulating B cells to produce antibodies.

There is a balance between the activities of the Th1 and Th2 cells in a normal human body. An excess of Th1 cell activity may be the result of an autoimmune disease, or the result of an ongoing infection. In the normal case, the Th1 cell activity diminishes when the physiological need thereof is reduced. An excess activity is thus seen when the normal reduced level of Th1 cell activity is not achieved as a response to the diminishing presence of the agent that induced the reaction, e.g. the starting point of an autoimmune disease.

Immune modulation aims at altering the balance between different subsets of responding T cells so that damaging responses are suppressed In many cases autoimmune diseases and intracellular infections are associated with the activation of Th1 cells, which activate macrophages and drive an inflammatory immune response. The drugs currently used to suppress the immune system can be divided into three categories:

1) Powerful anti-inflammatory drugs of the corticosteroid family such as prednisone. Glucocorticoids influence virtually every cellular and humoral mechanism related to inflammation and immune response. However, there are also many adverse effects, including fluid retention, weight gain, diabetes, bone mineral loss and thinning of the skin.

2) Cytotoxic drugs such as azthioprine and cyclophosphamide. Cytotoxic drugs cause immunosuppression by killing dividing cells and they have serious side-effects. The use of these compounds is limited due to a range of toxic effects on tissues that have continuous cell dividing, such as the bone marrow.

3) Cyclosporin A, tacromycin and rapamycin are powerful immunosuppressive agents that interfere with T-cell signaling.

All of these drugs are very broad in their action and inhibit protective functions of the immune system as well as pathological responses that cause tissue injury. Opportunistic infection is therefore a common complication of immune suppressive drugs.

It would be desirable to have an immunosuppressive agent that targets the specific part of the immune response that causes tissue injury. In particular, it would be desirable to obtain a medicament for suppression of harmful, i.e. excessive, Th1 cell mediated immune responses and simulation of Th2 cell mediated immune responses in a patient during ongoing infection and/or inflammation in said patient.

DESCRIPTION OF THE INVENTION

The present invention provides a medicament for suppression of excessive Th1 cell mediated immune responses and stimulation of Th2 cell mediated immune responses in a patient during ongoing infection and/or inflammation in said patient.

One aspect of the invention is directed to the use of at least one type of xanthophylls for the production of a medicament for suppression of excessive Th1 cell mediated immune responses and stimulation of Th2 cell mediated immune responses in a patient during ongoing infection and/or inflammation in said patient.

In a preferred embodiment of the invention the excessive Th1 cell mediated immune responses are caused by at least one disease from the group of autoimmune diseases and chronic viral and intracellular bacterial infections.

Examples of diseases that cause excessive Th1 cell mediated immune responses are Psoriasis vulgaris, Multiple sclerosis (MS), Reumatoid arthritis, Crohn's disease, Insulin-dependant diabetes mellitus, Tubercolosis (TB), Acute graft-versus-host disease (transplant rejection) and HIV virus infection Xanthophylles, including astaxanthin, is a large group of carotenoids containing oxygen in the molecule in addition to carbon and hydrogen. The carotenoids are produced de novo by plants, fungi and some bacteria [Johnson E. A. and Schroeder W. A., 1995, Adv In Biochem Engin. Biotechn 53: 119–178].

In a preferred embodiment of the invention, the type of xanthophyll is astaxanthin, preferably in a form esterified with fatty acids.

In a particularly preferred embodiment the astaxanthin is derived from a natural source, such as a culture of the algae Haemotococcus sp., e.g. *Haemotococcus pluvialis*.

The medicament in the invention is preferably an oral preparation, which optionally comprises an oil of food grade and it is suitably presented in separate unit doses.

The medicament may comprise a mixture of different types of xanthophylls or different forms of the same xanthophyll, such as a mixture of synthetic astaxanthin and naturally produced astaxanthin.

The oral preparation may comprise in addition to the xanthophylls auxiliary ingredients that are pharmacologically acceptable inactive or active ingredients, such as flavoring agents, fillers, emulsifiers, etc.

Examples of separate unit doses are tablets, gelatin capsules and predetermined amounts of solutions, e.g. oil solutions, or emulsions, e.g. water-in- oil or oil-in-water emulsions.

Another aspect of the invention is directed to a method of suppressing excessive Th1 cell mediated immune responses and stimulating Th2 cell mediated immune responses in a patient during ongoing infection and/or inflammation in said patient comprising administration of an Th1 cell response suppressing and Th2 cell response stimulating amount of at least one type of xanthophylls to said patient.

The examples and preferred embodiments described for the use aspect of the invention also apply for this method aspect of the invention.

In particular, excessive Th1 cell mediated immune responses are caused by at least one disease from the group of autoimmune diseases and chronic viral and intracellular bacterial infections, such as Psoriasis vulgaris, Multiple sclerosis (MS), Reumatoid arthritis, Crohn's disease, Insulin-dependent diabetes mellitus, Tubercolosis (TB), Acute graft-versus-host disease (transplant resection) and HIV virus infection, and the type of xanthophyll is preferably astaxanthin, particularly in a form esterified with fatty acids, e.g. from a natural source, such as a culture of the algae Haematococcus sp.

The daily doses of the active ingredient of the invention will normally be in the range of 0.01 to 10 mg per kg body weight for a human calculated on the amount of astaxanthin, but the actual dose will depend on the immune response of the individual human patient, the reason for suppression of the excessive Th1 cell mediated immune response, such as the type of disease causing the enhanced pathological Th1 cell response, and the recommendations of the manufacturer.

The xanthophyll astaxanthin is commercially produced via culturing of the algae Haematococcus sp. by AstaCarotene AB, Gustavsberg, Sweden. It is marketed and sold in Sweden as a dietary supplement Astaxanthin from other sources, and other xanthophylls as well, are expected to be similarly useful for the purposes of the invention. An advantage of using astaxanthin from algae is, however, that the astaxanthin exists in a form esterified with fatty acids [Renström B. et al, 1981, Phytochem 20(11):2561–2564], which esterified astaxanthin thereby is more stable during handling and storage than free astaxantin.

The naturally produced astaxanthin can be obtained also from fungi and crustaceans, in addition to from algae [Johnson E. A. and Schroeder W. A., ibid].

Case Studies

During the last five years reports have been received from patients taking the commercial dietary supplement capsules of the algal meal of *Haematococcus pluvialis*, Astaxin®, containing 4 mg astaxanthin. The daily doses recommended as an antioxidant is one capsule per day. However, 2–6 times that dose has been used by some patients without adverse effects. On the contrary, the higher doses have been experienced as beneficial in alleviating symptoms associated with some chronic diseases.

Six patient histories are disclosed more in detail below.

Chron's Disease

Patient 1. Boy, 17 years old, who had suffered from Crohn's disease for at least four years. He has been treated with anti-inflammatory agents, such as cortisone. He started to take the commercial product Astaxin (two capsules, each containing 4 mg of astaxanthin, per day). In about two months the cortisone treatment was phased out and later on stopped altogether. The patient was asymptomatic for more than a year when he experienced a relapse. He was then received a short-term treatment with cortisone in combination with Astaxin, and the cortisone treatment was again phased out.

Patient 2. Woman, about 50 years of age, who had suffered from Crohn's disease for a long time. She received treatment with cortisone. Now she has started to take Astaxin in parallel with her steroid medication and she reports that she feels considerably better.

Patient 3. Man, 48 years old, who has suffered from Crohn's disease for the last 20 years. He has been operated on several times and he has been treated with cortisone. Directly after the last operation he started taking Astaxin (6 capsules per day) and no cortisone. With regard to the circumstances, he has been asymptomatic. He has compared his clinical status after the operation with the status of two other patients who were operated on at the same time and who received conventional treatment with cortisone. In comparison with these two other patients his recovery has been fully equal with theirs, with the positive exception that edema in his colon diminished more quickly than in the two other patients.

Lichen Ruber Planus.

Patient 4. Woman, more than 70 years of age, who had suffered from the disease for several years. The symptoms of the disease were inter alia open wounds which had not healed She had been treated with anti-inflammatory agents, such as cortisone, for several years, orally and also by injection directly to the local inflammation areas. The treatment has not led to any result. She started to take 4 capsules of Astaxin per day, and after some weeks visible alleviation of the symptoms started to show up. The wounds were healed in slightly more than one month. During this period, the patient herself phased out the cortisone treatment. The dose of Astaxin was lowered to 2 capsules per day when she was asymtomatic. However, the symptoms returned in connection with a common cold. The dose was then increased to 4 capsules per day and the wounds healed again. She says herself that she now feels considerably better.

Psoriasis.

Patient 5. Male, 40 years, who suffers from psoriasis and mainly shows itself in rough skin on the elbows. After treatment with a skin cream enriched with alga meal/astaxanthin (100 mg astaxanthin/kg cream) twice a day for three weeks, the symptoms diminished.

Patient 6. Woman, 45 years old, who suffers from psoriasis and mainly shows itself in rough skin on the elbows. After treatment with a skin cream enriched with algal meal/astaxanthin (100 mg astaxanthin/kg cream) twice a day for three weeks, the symptoms diminished.

Thus, positive reports have been received from several patients suffering from Crohn's disease, rheumatoid arthritis, psoriasis and lichen planus. All of these diseases are autoimmune diseases which are known to be Th1 cell mediated diseases.

Therefore it is likely that the Th1 mediated response in the patients has been suppressed and that there is a shift of the Th1/Th2 balance of the immune response towards the Th2 response. Further, it is likely that patients suffering from other predominantly Th1 cell mediated diseases would benefit from suppression of excessive Th1 cell responses and stimulation of Th2 cell mediated immune responses during ongoing infection and/or inflammation

What is claimed is:

1. A method of suppressing excessive Th1 cell mediated immune responses and stimulating Th2 cell mediated immune responses in a patient with Crohn's disease during ongoing infection and/or inflammation in said patient comprising administration of an Th1 cell response suppressing and Th2 cell response stimulating amount of at least one type of xanthophylls to said patient.

2. The method according to claim 1, wherein the type of xanthophyll is astaxanthin.

3. The method according to claim 2, wherein the astaxanthin is in a form esterified with fatty acids.

4. The method according to claim 2, wherein the astaxanthin is derived from a natural source.

5. The method according to claim 4, wherein the natural source is a culture of the algae Haematococcus sp.

6. The method according to claim 3, wherein the astaxanthin is derived from a natural source.

7. The method according to claim 6, wherein the natural source is a culture algae Haematococcus sp.

* * * * *